US007903251B1

(12) United States Patent
Farr et al.

(10) Patent No.: US 7,903,251 B1
(45) Date of Patent: Mar. 8, 2011

(54) REPRESENTATION OF SPATIAL-FREQUENCY DATA AS A MAP

(75) Inventors: Lance W. Farr, Hereford (GB); Timothy W. James, Reynoldston (GB); Jonathan N. Stearn, Llandovery (GB)

(73) Assignee: Acuitas Medical Limited, Swansea, Wales (GB)

( * ) Notice: Subject to any disclaimer, the term of this patent is extended or adjusted under 35 U.S.C. 154(b) by 0 days.

(21) Appl. No.: 12/710,065

(22) Filed: Feb. 22, 2010

Related U.S. Application Data

(60) Provisional application No. 61/154,030, filed on Feb. 20, 2009.

(51) Int. Cl.
G01N 21/55 (2006.01)
G01N 21/25 (2006.01)
(52) U.S. Cl. .......... 356/448; 356/407; 356/408; 356/433
(58) Field of Classification Search .......... 356/445–448, 356/432–435, 402–410, 451, 326, 328, 318; 250/226, 234
See application file for complete search history.

(56) References Cited

U.S. PATENT DOCUMENTS

| 5,050,990 | A | * | 9/1991 | Smith et al. | 356/326 |
| 5,359,434 | A | * | 10/1994 | Nakao et al. | 358/481 |
| 6,205,259 | B1 | * | 3/2001 | Komiya et al. | 382/284 |
| 7,466,421 | B2 | * | 12/2008 | Weitzel | 356/451 |
| 2006/0155186 | A1 | | 7/2006 | James | |
| 2007/0167717 | A1 | | 7/2007 | James et al. | |
| 2009/0284713 | A1 | * | 11/2009 | Silverstein et al. | 353/8 |

\* cited by examiner

Primary Examiner — Sang Nguyen
(74) Attorney, Agent, or Firm — Blakely Sokoloff Taylor & Zafman LLP

(57) ABSTRACT

A method for representing the structural information in a biological or physical sample is disclosed. In this method, a time-frequency representation of the spatial distribution within a sample is transformed into a color representation of the data. Furthermore, due to the directional sensitivity of the method for gathering the data, information about the structural anisotropy of the sample can also be encoded from the data. The application of this method to one or more regions within the sample enables a map to be generated which clearly illustrates quantitative measures of the structures present.

3 Claims, 5 Drawing Sheets

Red channel of RGB color map

Green channel of RGB color map

Blue channel of RGB color map

The color assigned to a given point encodes the structural information in a region around that point Green channel of RGB color map with prisms running horizontally

Green channel of RGB color map with prisms running vertically

REPRESENTATION OF SPATIAL-FREQUENCY DATA AS A MAP

CROSS-REFERENCE TO RELATED APPLICATION

This application claims the benefit of U.S. Provisional Patent Application No. 61/154,030 filed Feb. 20, 2009.

BACKGROUND OF THE INVENTION

1. Field of the Invention

The present invention relates to the field of diagnostic assessment and monitoring of complex biological and physical structures, including, but not limited to, regions of the body which experience a change in structure. The change in structure includes, but is not limited to, changes during disease (e.g., angiogenesis) or changes between different functional modes (e.g., mammary glands before, during and after pregnancy).

2. Prior Art

Glossary: The following terms will be used throughout the text.

1. Prism: A prism is an elongate volume of material from which a signal is measured. The signal varies as a function of position along the prism. Although the form of prism generally referred to in the text has a rectangular cross section, in general it may include shapes of any arbitrary cross-section. Additionally, although the measurement of signal generally referred to in the text is a modification of current MRI techniques, as it is evident to anyone skilled in the art, the signal could also be gathered from a prism volume using other techniques.
2. Profile: A profile is the signal as a function of position along a single direction within a prism. Profiles taken from materials with heterogeneous signal intensity will in general be non-constant and represent a measure of the amount of signal generating material with position in the prism. As an example, this may be presence or absence of material, or material density. However, it could measure any number of properties of the material, but the salient point that the signal versus position gives a measure of some physical property with position along the prism. As is evident to one skilled in the art, the profile could represent any measurable physical property which varies with position.
3. Segment: In order to perform measurements on the variation of the profile signal with position, a portion of the profile of finite extent is used. This portion of profile may be less than or equal to the entire profile length, and is termed a "segment".
4. Spatial frequency: In signal processing, many techniques exist for estimating the frequency content of a signal. Generally these signals vary with time. When these techniques are applied to a signal which varies with position, rather than time, the analogue of frequency content is a measure of the frequency of spatial variations along the profile. For the purposes of this discussion, this will be termed the "spatial frequency".
5. Spatial frequency spectrum: A spatial frequency spectrum is a representation of the spatial frequency content of a segment of a profile. It graphically illustrates the relative or absolute amounts of signal present in the segment as a function of spatial frequency.
6. Color frequency: A color frequency is a frequency of visible light, which has an associated wavelength, and therefore color, when viewed by a human on a display device. Color frequencies form a continuum of distinct colors.
7. Color frequency spectrum: For a given point on a display device, the final color displayed can be formed from a combination of one or more color frequencies. The color frequencies and their associated intensities (absolute and relative) determine the perceived color and brightness of that point on the display. Differing color spectra displayed at different points on the display device will therefore generally have differing perceived color and brightness, indicating differences in the underlying color frequency spectra.
8. Bin: When encoding spatial frequency spectra as color frequency spectra, groups of spatial frequencies may be grouped together by combination of their associated magnitudes (an example of this would be summation of the magnitudes), and each grouping of spatial frequencies forms what is termed a "bin".
9. Color map: A color map is a one or more dimensional plot, in which color is assigned to points within the plot. In the case of the preferred embodiment described herein, this may take the form of a two-dimensional plot where the color frequencies are used to encode spatial frequencies.

Biological structures can change size, shape or arrangement when changing from non-diseased to diseased states, or when changing between different functional modes. Many of these structures are of great clinical interest. For example, during angiogenesis, the number and spacing of blood vessels changes, and the blood vessels can take on a different arrangement to that in normal tissue. The ability to interrogate these structures rapidly and in-vivo is a highly desired capability. Similarly, physical structures, such as rock strata, can also experience change in structure, either spatially or temporally.

In the case of anatomical structures, for example mammary ducts or blood vessels, the sizes of many of these structures of interest can be very small and difficult or impossible to image using current in-vivo imaging techniques, for example Magnetic Resonance Imaging (MRI).

MRI, which is inherently a three-dimensional technique, is well suited to the determination of the structural details which will, in general, vary in three-dimensions. Thus, the ability to quantify and display these structures in three-dimensions is a desirable capability.

However, high resolution MRI images, which would be necessary to measure many smaller physical and biological structures, require careful patient positioning and stabilization, as well as lengthy exam times. Furthermore, high-field systems may be required. These high-field systems cost around $2 million and need to be housed in carefully controlled environments overseen by radiology specialists.

MRI is based on an extension of the mathematics of Fourier expansion which states that a one-dimensional repetitive waveform (e.g., a signal amplitude as a function of linear position) can be represented as the sum of a series of decreasing period (increasing frequency) sinusoidal waveforms with appropriate coefficients (k-values).

In MRI, the item (body part) to be imaged is a three-dimensional object. The basic concept of k-values in one dimension can be extended to two or three dimensions. Now, rather than a series of k-values, there is a two- or three-dimensional matrix of k-values, each k-value representing a particular spatial frequency and direction in the sample.

In Fourier analysis, converting from the k-values to the desired waveform (amplitude vs. time for a time-varying signal or image intensity vs. position for the MRI case) is accomplished by using a Fourier transform. The Fourier transform in simple terms is a well-known means to convert between the frequency domain and time domain (for time-varying signals). For images, as in the MRI case, the Fourier transform is used to convert between the spatial frequency domain (the series of sinusoidal waveforms and their coefficients, referred to as k-space) and the spatial arrangement of signal intensities for each of the imaged volumes (voxels). Similar to the case of time-varying signals, where the k-values are the coefficients for the sinusoidal waveforms with given periods, the k-values in the MRI case are the coefficients for the sinusoidal waveforms with given wave lengths (where the wavelengths are inversely related to spatial frequencies, i.e., a long wavelength is a low spatial frequency).

MRI technology today uses a number of methods to acquire images. Virtually all rely on gathering the k-space coefficients and later Fourier transforming them into an image (or set of images as in a 3D acquisition). In the simplest abstraction, this is accomplished by placing the part to be imaged in a strong magnetic field and exciting the hydrogen nuclei in the sample by transmitting at the sample a pulsed radio-frequency electromagnetic signal tuned to the resonant frequency of the hydrogen nuclei. This pulse starts the nuclei resonating at their resonant frequency. Then, to obtain information about where in the sample the signal originates from, the spins of the excited hydrogen atoms are encoded with a combination of phase and frequency encodes corresponding to the desired k-space data being acquired on that excitation. (Here phase and frequency correspond to the resonant frequency and phase of the hydrogen nuclei). This is accomplished by modulating the magnetic field spatially and temporally, so as to correspondingly spatially alter the resonant frequency of the nuclei and modulate their phase. A signal is received back then from the excited hydrogen nuclei of the sample, and the k-space values are extracted from the signal. This process of excitation, encoding, and signal acquisition is repeated until an entire matrix of k-space values (properly selected to constitute a Fourier series) is acquired with sufficiently high spatial frequency to resolve the desired features in the sample. Finally, the matrix of k-values is Fourier transformed to produce an image or images. There are many variations and extensions of this theme in use in current technology MRI systems. One approach utilizes frequency encoding to generate the k-values for each of these 2D slices.

In signal processing, techniques exist for measuring the spectral content of a time-varying signal, called time-frequency representations. One such example of this is a spectrogram. In a spectrogram, a plot of how the spectral density varies with time along the signal is generated. The spectral density measurement is created either by a series of bandpass filters, or more often by application of the short-time Fourier transform (STFT) to the signal. In the case of the STFT method, the spectral density displayed for a given time point is usually derived from the Fourier transform of a region (segment) extending over a period of time to either side of this.

U.S. Patent Application Publication Nos. US-2006/0155186-A1 and US-2007/0167717-A1 describe techniques for generating spatial frequency spectra from specific locations and directions in a three-dimensional sample using MRI techniques. These two patent applications are incorporated herein by reference.

U.S. Patent Application Publication No. US-2007/0167717-A1 describes a method for acquiring spatial frequency spectra from specific locations in a three-dimensional sample using modifications of the current MRI techniques for localized NMR spectroscopy. The innovation, in its simplest abstraction, is to add the use of a read out gradient to the current NMR spectroscopy pulse sequences and record the resultant echo for subsequent spatial frequency analysis. These techniques generate spectra from a selected region or generate an image of the results over a region of the sample. These methods can be applied to analyzing the structure of trabecular bone as well as for analyzing or diagnosing disease in cases where there is a difference in the spatial frequency power spectrum due to physiologic or disease processes. Various embodiments are disclosed. However, that application does not disclose the encoding of the spatial frequency power spectrum into color frequencies, which may then be plotted as a "color map". That application also does not include application of this to one or more volumes within the sample to generate an image representation of a structure or structures of interest. Furthermore, that application does not include the use of multiple color maps running through the same region, but in different directions and/or at later time points, which would allow information about the anisotropy and time-evolution of a structure to be readily assessed and visualized in a desirable way.

Mapping of spatial frequency data is not currently performed, and thus there is no prior art.

DETAILED DESCRIPTION OF THE PREFERRED EMBODIMENTS

Figure 1:
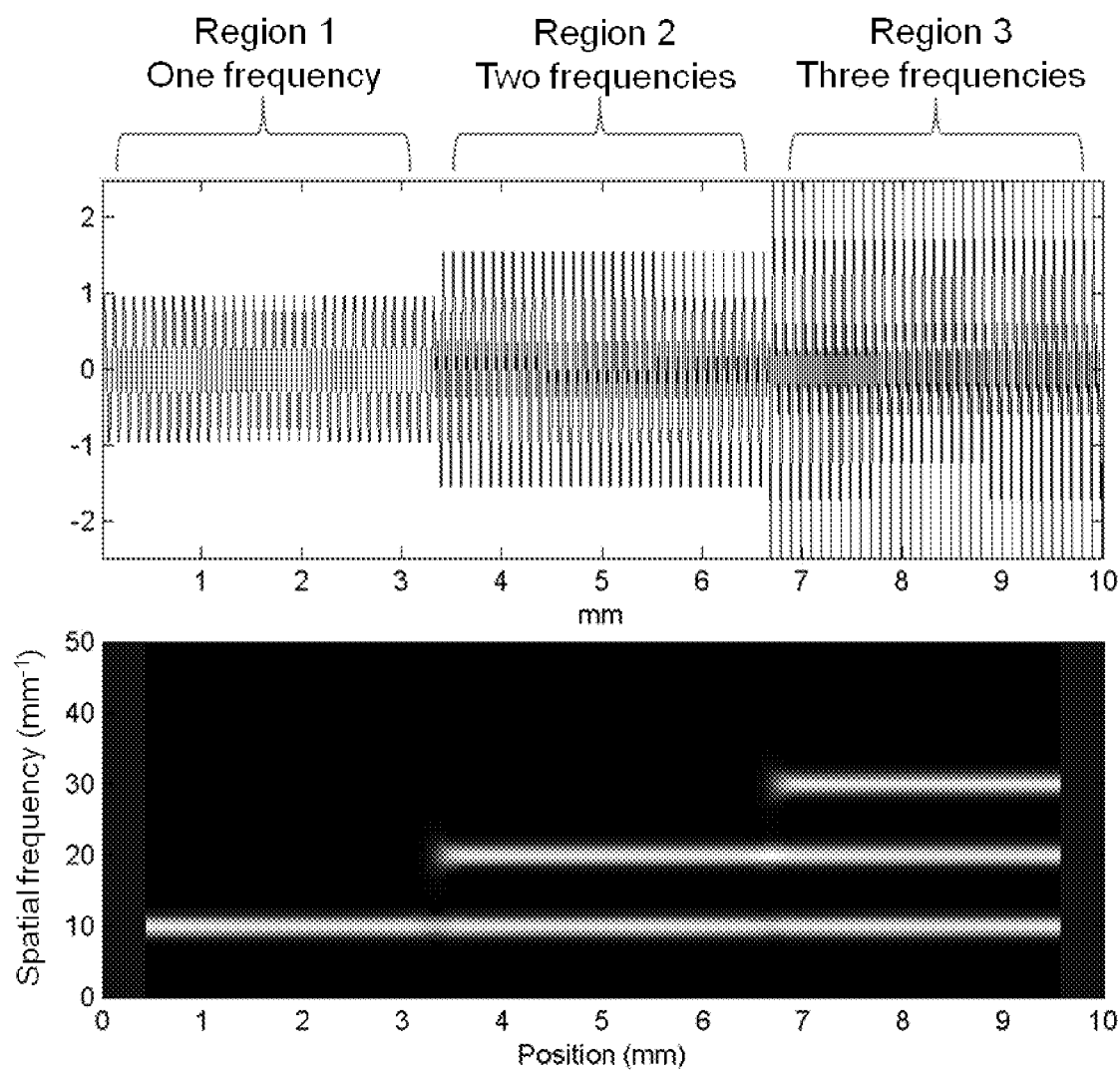
FIG. 1 shows a signal and its associated spectrogram. The signal contains three distinct regions. Region 1 contains only one frequency, region 2 contains a combination of 2 different frequencies and region 3 contains a combination of 3 different frequencies. The spectrogram indicates the spatial distribution of frequencies, and the regions with 1, 2 and 3 different frequencies are clearly indicated.

As noted above, this application claims priority on one provisional application. This provisional application describes a method for representing the structural information in a biological or physical sample. In this method, a time-frequency representation of the spatial distribution within a sample is transformed into a color representation of the data. Furthermore, due to the directional sensitivity of the method for gathering the data, information about the structural anisotropy of the sample can also be encoded from the data. The application of this method to one or more regions within the sample enables a map to be generated which clearly illustrates quantitative measures of the structures present.

In the preferred embodiment, the method disclosed in U.S. Patent Application Publication No. US-2007/0167717-A1 is used to produce a measure of the signal generating material present versus position along a direction within a sample volume of material, herein referred to as the "prism". In the preferred embodiment this sample volume may be a rectangular stick or rod, although in practice a volume forming any shape could potentially be used. In the preferred embodiment this measurement is performed using a modification of current MRI techniques, however as it is evident to anyone skilled in the art, the following analysis could also be performed on information gathered about the spatial distribution of structures within a prism volume using other techniques.

In practice, the measurement of the amount of material with position in the volume gives a signal which varies with position in the volume. The magnitude of this signal represents some measure of the material contained within the prism. As an example, this may be presence or absence of material, or material density. However, it could measure any number of properties of the material, but the salient point that the signal versus position gives a measure of some physical property with position along the prism. This signal versus position is termed a "profile", and as evident to anyone skilled in the art, it could represent any measurable physical property with position. In the preferred embodiment this measure would be magnetic resonance signal intensity with position along the prism.

In general, signal processing techniques measure the variation of some signal with time. They can be used to select a region of the signal, which can be less than the length of the entire signal, and interrogate the signals within this region. The region for which this interrogation is performed is termed the "region of interest" or "ROI". In the case of profile data, the variation of signal occurs with position, not time, although the same techniques can be readily applied to this information. In signal processing, many techniques exist for estimating the frequency content of a signal. When these techniques are applied to a signal which varies with position, rather than time, the analogue of frequency content would be a measure of the frequency of spatial variations along the profile. For the purposes of this discussion, this will be termed the "spatial frequency". The techniques used to estimate the frequency content of a signal generally produce some measure of the distribution of frequencies present in the signal, or an estimation of the amount of signal present at a given frequency. In the preferred embodiment, a measure of the spatial frequency content of the profile is generated, by the application of signal processing techniques, which give an estimate of the amount and distribution of spatial frequencies present in a region of the profile. This estimate of amount and distribution of spatial frequencies is termed a "spatial frequency spectrum".

The present invention is a far simpler and more elegant solution for visualizing physical or biological structures than the prior art. By way of example, this includes structures within the body.

In this embodiment, a time-frequency representation (e.g., a spectrogram) is used to represent the profile data. In a spectrogram, a plot of how the spectral density varies with distance along the profile is generated. As MRI data is generally represented digitally, the preferred method of measuring the spectral density would be through the calculation of the short-time Fourier transform (SIFT) from the profile. An example spectrogram is shown in FIG. 1. The analogue of a time-varying signal in this application is the profile, which varies with distance. In this case the time-frequency representation indicates the variation of spectral density with distance along the profile.

Figure 2:
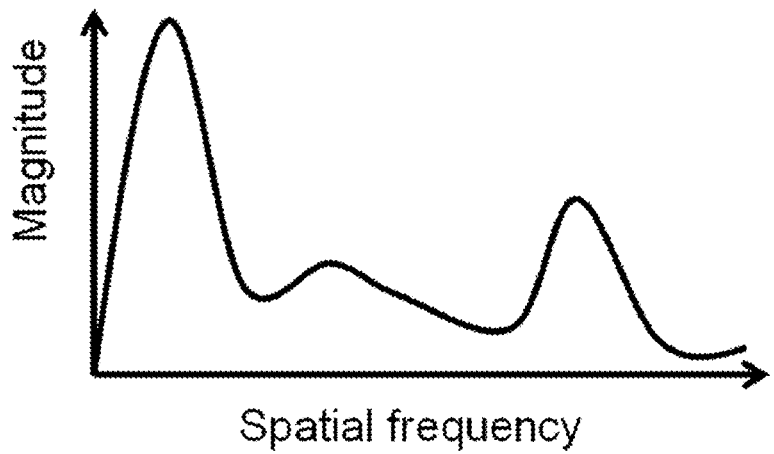
FIG. 2 shows an example spatial frequency spectrum.
Figure 3:
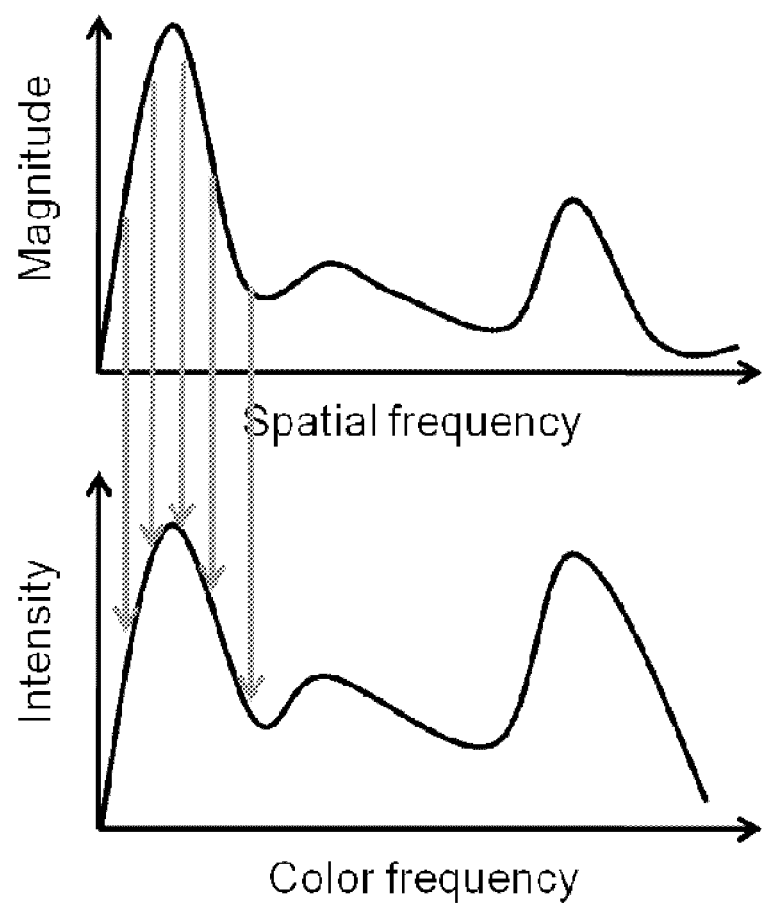
FIG. 3 shows a diagram illustrating the encoding of spatial frequency data into color frequency data. The color frequencies used are in the visible range, such that they can be displayed for human interpretation. The transfer function itself can be any desired transfer function e.g., assignment of a particular color to a frequency or range of frequencies that represent a disease process.

Thus, each point along the distance-axis of the spectrogram indicates the spectral density in a region of material of a certain extent around that point. In its most general form, each point along the profile will have a spatial frequency spectrum consisting of a series of "spatial frequencies", each with an associated "magnitude" indicating the relative or absolute proportion of structures present at that spatial frequency value. This is illustrated in FIG. 2. In order to display this large amount of data in a meaningful way, spatial frequencies are assigned corresponding "color frequencies", and a transfer function is used to encode each spatial frequency "magnitude" data point as a color frequency "intensity". This is illustrated in FIG. 3. The combination of these color frequencies, weighted by their associated intensities, gives a final composite color value which is representative of all of the spatial frequencies for that position along the distance-axis of the spectrogram. This is performed for each increment along the profile to generate a linear plot of color versus distance.

The spatial frequency spectrum may be encoded into color frequencies in a number of ways, including: a) encoding each spatial frequency into a given color frequency such that there are the same number of color frequencies as spatial frequencies), b) the number of color frequencies may be decreased by combining groups of spatial frequencies into a smaller number of groups of spatial frequencies, termed "bins", or c) using a subset of spatial frequencies (either a consecutive subset or selected ones distributed throughout the range of spatial frequencies) instead of the full set and assigning color frequencies to these.

The intensity of the color frequency corresponding to a given spatial frequency is calculated from the relative or absolute value of the spatial frequency spectrum magnitude at the given frequency. The transformation of spatial frequency magnitude to color frequency intensity may be linear, or may have a different transfer function. Additionally the individual color frequencies may have identical or differing transfer functions to each other. The set of transfer functions would be varied to enhance the representation of spatial frequency data depending upon the particular structure being investigated.

The composite color derived from the spatial frequency spectrum of a segment of the profile can be displayed in a number of ways including; a) assigned to the point along the profile at the mid point of the segment used to generate the spatial frequency spectrum, b) assigned to a range of points along the profile with intensity weighted to indicate the extent of the segment used to generate the spatial frequency spectrum (e.g., weighted by the same window function used for the frequency analysis).

One or more prisms may be analysed in this way, arranged so as to provide sufficient coverage of the region of interest. This includes, but is not limited to, arrays of parallel prisms, either overlapping or not overlapping, or prisms positioned at various angles through a region of interest.

Figure 4:
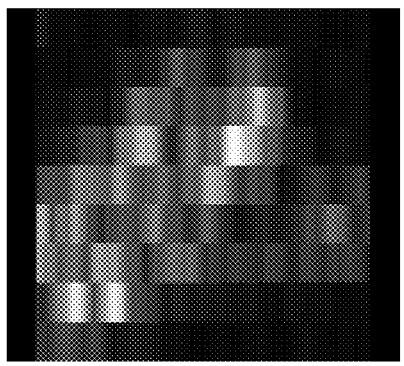
FIG. 4 shows the red, green and blue color channels from a color map, illustrating the structural information encoded in the generated image. In this case the data is from a set of nine parallel horizontal prisms.
Figure 4:
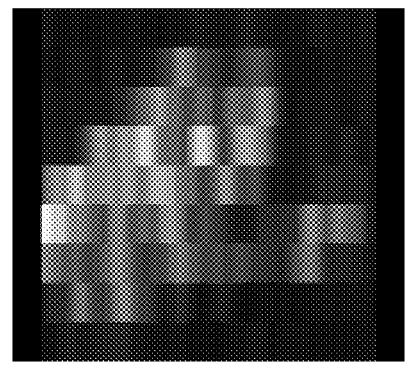
Figure 4:
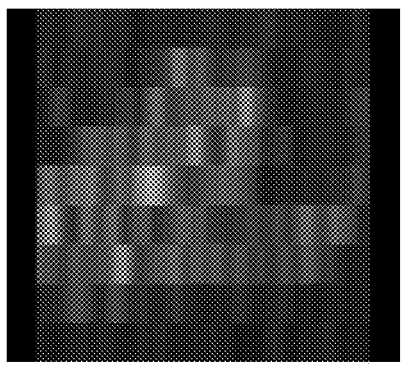
Figure 5:
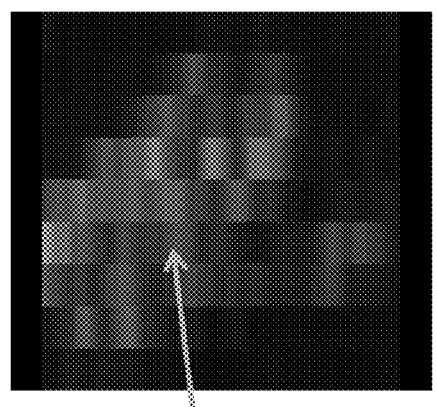
FIG. 5 shows an example color map (re-colored in grayscale). The figure illustrates that the color at any given point encodes the structural information in a region around that point.

The assignment of colors to the spatial frequency data allows a "color map" to be generated which allows the spatial distribution of the spatial frequency data to be interpreted with reference to anatomical features of interest. An example of the red green and blue channels from a color map is shown in FIG. 4.

Figure 6:
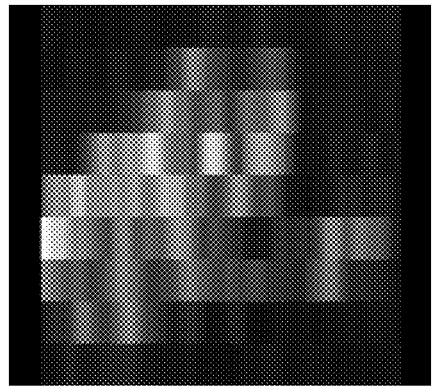
FIG. 6 shows the green channel from two color maps of the same region, but with prisms running in different directions in each case. The difference in color at equivalent locations in each map indicates the anisotropy of the structures present in that location.
Figure 6:
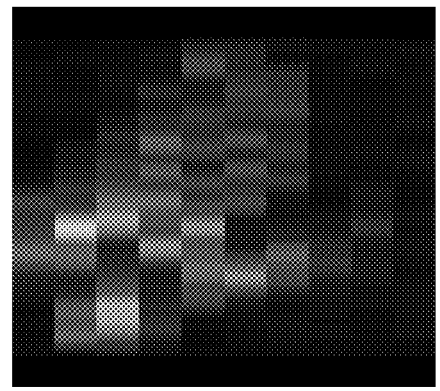

The spatial frequency analysis technique is sensitive to direction. Therefore, in the case of prisms passing through the same region of interest, but at differing angles, the information about the spatial frequency distribution with angle through a given region can then be ascertained by the appropriate analysis and interpretation of this data. Biological or other structures may be anisotropic, and thus this method may give useful information about the structural anisotropy in a given anatomical region (diseased or otherwise). An example of the way anisotropy can be highlighted by this method is shown in FIG. 6.

Subsequent sets of 1 or more prisms can then be gathered through the same anatomical region. In general, the further sets of prisms(s) can be oriented at various angles to the initial set. By gathering the data at subsequent time points, a color map can then be generated at each time point at which data was gathered, and the data displayed as a series of images or a video animation. This would allow the changes in structure over time to be visualized.

Figure 7:
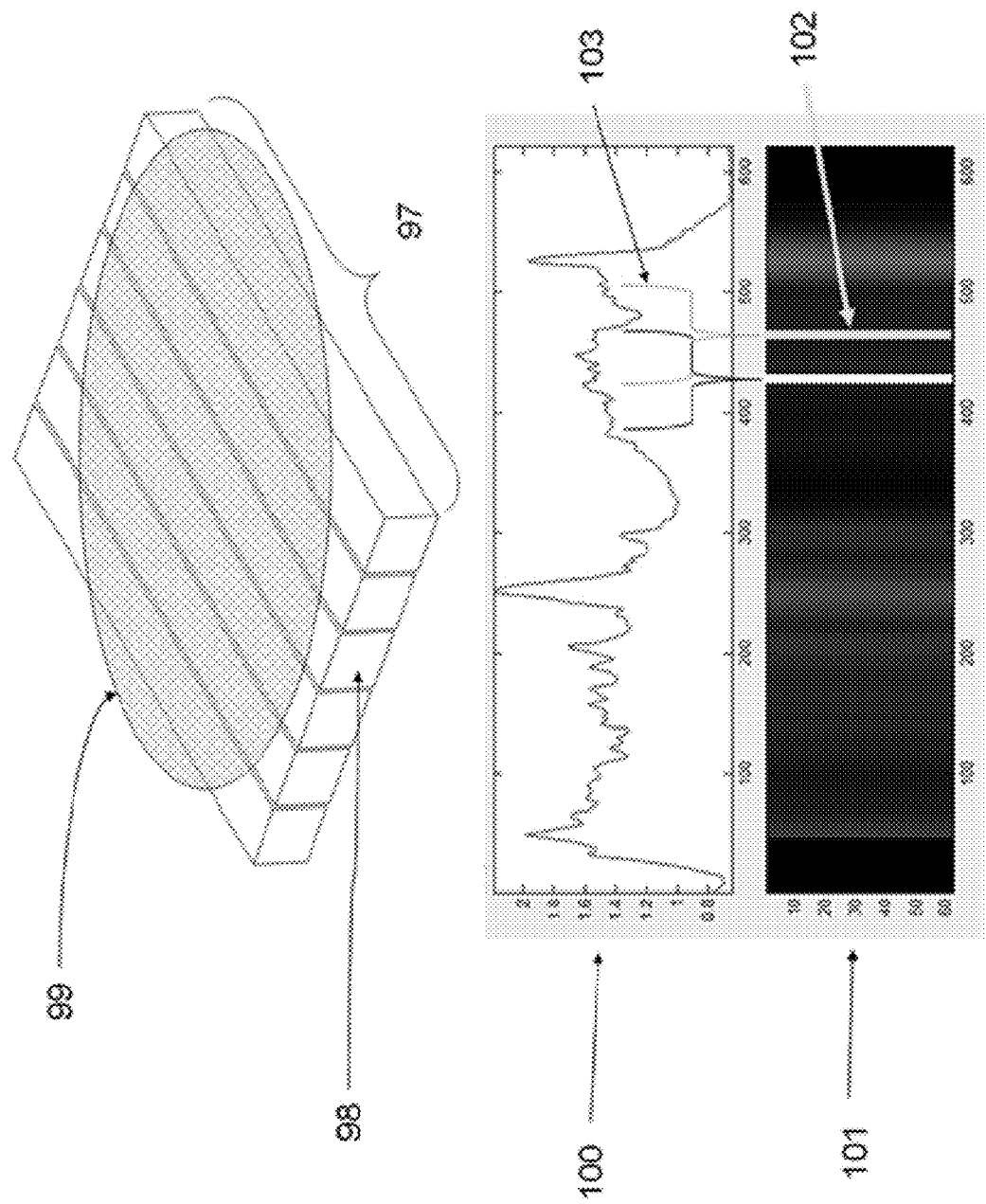
FIG. 7 shows a set of prisms (98) running through a sample of material (99). The profile along the length (97) of one of the prisms is given in (100). The assignment of a representative composite color (102) from different segments (103) of the profile enables a color map (101) to be generated.

The following is a step by step description of the method to generate a spatial frequency color map with hue and intensity representing spatial frequencies and their magnitudes respectively as a function of location in a specimen. This brief description illustrates a basic implementation of the method. With reference to FIG. 7, the first step is to acquire signal magnitude versus position (profiles) along one or an array of prisms (97, 98). In FIG. 7 the array is shown as a parallel array of adjacent prisms with a square cross section. In general the prisms could be of any arbitrary cross section and arrangement chosen to appropriately cover the region of the specimen for analysis (99). The next step is to analyze multiple segments of each of the profiles (100). The segment length (103) is in part chosen to be long enough for the desired structural features to be seen (e.g., longer than their wavelength), but shorter than the prism(s).

Figure 8:
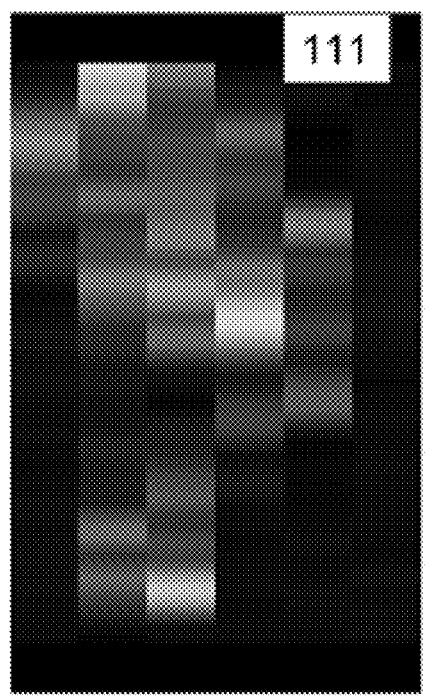
FIG. 8 shows a color map (111) and its associated reference image (110).
Figure 8:
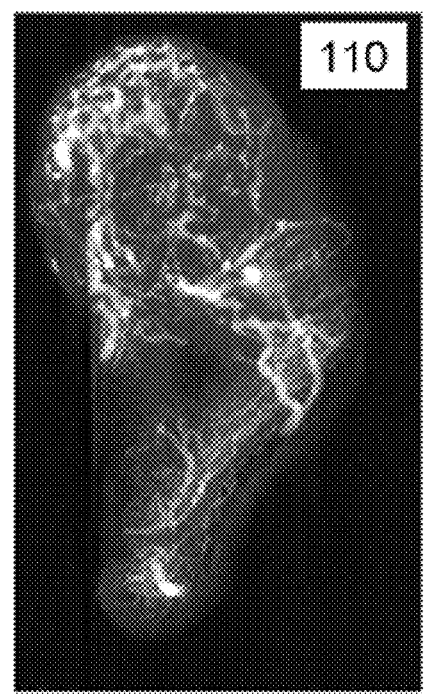

Using the chosen segment length, spatial frequency analysis is then preformed on as many adjacent or overlapping segments as desired to display the distribution of spatial frequencies in each segment of the region of the specimen for analysis (99). For each of these segments, a distribution of colors is associated with the range of spatial frequencies, each color to a respective frequency, and an intensity of each color is associated with the magnitude of the respective spatial frequency. Then a polychromatic color and intensity is computed based on a transfer function. The polychromatic color and its intensity will represent a combination of the colors and the magnitudes of the respective colors for each segment. With reference to FIG. 3, this transfer function can be of many forms. In this example, intensity at high spatial frequencies present in the spatial frequency spectrum contribute intensity to high frequency colors (e.g., blue) and low spatial frequencies contribute to low frequency colors (e.g., red) with a continuum in-between. Again with reference to FIG. 3, this produces a composite polychromatic color spectrum which is then displayed at the appropriate location along the prism (102) to produce a one dimensional color mapped representation of the distribution of spatial frequencies as a function of position along the prism (101). The illustration in FIG. 7 shows plotting the composite color at the mid point of the analyzed segment, alternatively the color could be plotted in a distributed fashion corresponding to the entire length of the analyzed segment. This could be in a weighted fashion such as maximum at the mid point and tapered in intensity towards the ends. A two dimensional map is then generated by arraying the one dimensional color mapped images (101) in proper relative relation so that the colors generate a map as illustrated in FIG. 8 (111). Alternatively, the composite color may be broken down into its color components, for providing a map for each color component, such as for each of three primary colors. The addition of a reference image (110) (magnetic resonance image or other modality) presented at the same scale and orientation as the color map provides a spatial reference for interpreting the color map(s) relative to the specimen being analyzed.

While certain preferred embodiments of the present invention have been disclosed and described herein for purposes of illustration and not for purposes of limitation, it will be understood by those skilled in the art that various changes in form and detail may be made therein without departing from the spirit and scope of the invention. It is therefore the intention that the appended claims be interpreted as broadly as possible in view of the prior art to include all such variations.

What is claimed is:

1. A method of obtaining, analyzing and representing data from a specimen comprising:
    acquiring from the specimen, signal magnitude versus position along a prism shaped region of the specimen;
    selecting a segment length that is longer than the structural features of the specimen desired to be analyzed and represented and shorter than the prism;
    using the chosen segment length, performing a spatial frequency analysis on each of adjacent or overlapping segments along the prism to obtain magnitude versus spatial frequency over a range of spatial frequencies in each segment;
    for each segment, associating a distribution of colors to the range of spatial frequencies and associating an intensity of each color with the magnitude of the associated spatial frequency;
    finding a polychromatic color having an intensity representing a combination of the colors and the respective magnitudes of the colors for each segment; and
    providing an output of the polychromatic colors versus position along the prism.

2. The method of claim 1 wherein the method is repeated for adjacent prisms.

3. The method of claim 1 wherein the output of the polychromatic colors versus position along the prism is provided by color components of the polychromatic colors versus position along the prism.

* * * * *